US008481970B2

(12) United States Patent
Cooper et al.

(10) Patent No.: US 8,481,970 B2
(45) Date of Patent: Jul. 9, 2013

(54) SANITIZER FOR PORTABLE ELECTRONIC DEVICES

(75) Inventors: Jonathan Cooper, Lloyd Harbor, NY (US); Robert E. Cannuscio, West Chester, PA (US)

(73) Assignee: Spectronics Corporation, Westbury, NY (US)

( * ) Notice: Subject to any disclaimer, the term of this patent is extended or adjusted under 35 U.S.C. 154(b) by 584 days.

(21) Appl. No.: 12/460,356

(22) Filed: Jul. 16, 2009

(65) Prior Publication Data

US 2010/0044582 A1 Feb. 25, 2010

Related U.S. Application Data

(60) Provisional application No. 61/189,488, filed on Aug. 19, 2008.

(51) Int. Cl.
*A61L 2/10* (2006.01)

(52) U.S. Cl.
USPC ............ 250/455.11; 250/453.11; 250/454.11; 250/494.1; 250/504 R; 422/20; 422/21; 422/22; 422/24

(58) Field of Classification Search
USPC ..................... 422/20, 21, 22, 24; 250/453.11, 250/454.11, 455.11, 493.1, 494.1, 504 R
See application file for complete search history.

(56) References Cited

U.S. PATENT DOCUMENTS

| | | | |
|---|---|---|---|
| 4,973,847 A | 11/1990 | Lackey et al. | |
| 5,845,504 A * | 12/1998 | LeBleu | 62/92 |
| 6,458,331 B1 * | 10/2002 | Roberts | 422/186.3 |
| 6,461,568 B1 | 10/2002 | Eckhardt | |
| 6,475,433 B2 * | 11/2002 | McGeorge et al. | 422/24 |
| 6,490,351 B1 | 12/2002 | Roberts | |
| 6,646,270 B2 | 11/2003 | Cunningham | |
| 6,953,940 B2 | 10/2005 | Leighley et al. | |
| 7,372,044 B2 | 5/2008 | Ross | |
| 2004/0147293 A1 * | 7/2004 | Park | 455/573 |
| 2006/0147339 A1 * | 7/2006 | Hunter et al. | 422/24 |
| 2006/0175554 A1 * | 8/2006 | Riddell | 250/455.11 |
| 2008/0067417 A1 * | 3/2008 | Lane et al. | 250/455.11 |
| 2008/0067418 A1 * | 3/2008 | Ross | 250/455.11 |
| 2008/0219883 A1 * | 9/2008 | Thur et al. | 422/22 |
| 2009/0218512 A1 | 9/2009 | Ranta et al. | |

OTHER PUBLICATIONS

Sonicare FlexCare toothbrush roasts germs with UV radiation, 3 pages, Jul. 2, 2008, http://dvice.com/archives/2007/06/sonicare_flexcare_toothbrush_r.php.

"Violight UV Cell Phone Sanitizer Will Kill Nasty Germs on Your Cellphone", 2 pages, May 29, 2009, http://chipchick.com/2009/05/violight_uv_cell_phone_sanitizer.html.

* cited by examiner

*Primary Examiner* — Nicole Ippolito
(74) *Attorney, Agent, or Firm* — Drinker Biddle & Reath LLP (57) ABSTRACT

A sanitizer for sanitizing a portable electronic device is provided, the sanitizer having a base including a cavity for receiving the electronic device, at least one ultraviolet radiation source for emitting ultraviolet radiation into the cavity, a cover cooperating with the base, the cover moving between an open position wherein the electronic device can be inserted into or removed from the cavity and a closed position wherein the cavity is enclosed so as to substantially maintain the ultraviolet radiation within the cavity, and a controller for enabling the ultraviolet radiation source to be activated only when the cover is closed.

37 Claims, 11 Drawing Sheets

SANITIZER FOR PORTABLE ELECTRONIC DEVICES

CROSS-REFERENCE TO RELATED APPLICATIONS

This application claims priority from U.S. Provisional Application No. 61/189,488 filed on Aug. 19, 2008, which is incorporated herein by reference in its entirety.

FIELD OF THE INVENTION

The invention relates devices and systems for sanitizing hand-held and portable electronic devices, including mobile (cellular) telephones, personal digital assistants (PDAs), portable music and video players (e.g., MP3 and MP4 players), portable cameras, portable global positioning devices, and the like.

BACKGROUND OF THE INVENTION

Portable electronic devices may become contaminated with bacteria or other infectious agents, and thus may be a medium for the transfer of infection from one user to another. Even when a device is used essentially only by a single user, if the device becomes contaminated, the user is exposed to the risk of infection for as long as the device remains contaminated.

Ultraviolet radiation in the 200-300 nanometer (nm) range is effective at killing microorganisms such as airborne and surface bacteria, viruses, yeasts, and molds. A germicidal effectiveness curve (based upon the effect of various wavelengths of radiation on a common bacterium) indicates a peak of photic absorption by the bacterial DNA at 254 nm. There are commercially available light sources that generate UV light in the wavelength range of about 200 nm to about 300 nm, which encompasses the effectiveness peak. Such light sources are used extensively in air and water purification applications in the food and beverage industry, in medical sterilization applications, drinking water purification, and sewage treatment.

While UV light is helpful in sterilizing surfaces, overexposure to short wave UV rays can be harmful to humans. Studies have shown ill effects of overexposure to UV rays found in solar energy. Similarly, overexposure to lamp-emitted germicidal UV radiation can cause erythema of the skin similar to sunburn, and direct exposure to the eyes can cause painful inflammation of the conjunctiva, cornea and iris, or even lasting damage. Persons working extensively with UV light generally are advised to wear special goggles or be shielded by non-UV transmitting protective plate glass. Children's skin and eyes are particularly sensitive to UV exposure. Therefore, measures need to be taken to reduce the risk of accidental or uninformed exposure to UV radiation.

In U.S. Pat. No. 6,953,940, the assignee of the present invention disclosed a device to sanitize dental equipment, such as toothbrushes, by exposing the equipment to ultraviolet radiation, commonly at a wavelength of about 254 nm.

However, there is a continuing need for a sanitizing device that is compact, safe, reliable, and efficient and which can be used for sanitizing handheld and portable electronic devices.

SUMMARY OF THE INVENTION

In one embodiment, a sanitizer for sanitizing a portable electronic device is provided. The sanitizer has a base including a cavity for receiving the electronic device, at least one ultraviolet radiation source for emitting ultraviolet radiation into the cavity, and a cover cooperating with the base, the cover moving between an open position wherein the electronic device can be inserted into or removed from the cavity and a closed position wherein the cavity is enclosed so as to substantially maintain the ultraviolet radiation within the cavity. The sanitizer has controller for enabling the ultraviolet radiation source to be activated only when the cavity is enclosed.

In another embodiment, the sanitizer has a base including a cavity for receiving the electronic device, wherein at least a portion of the cavity is lined with a reflective surface, at least one ultraviolet radiation source for emitting ultraviolet radiation into the cavity, and a cover cooperating with the base, the cover moving between an open position wherein the electronic device can be inserted into or removed from the cavity and a closed position wherein the cavity is enclosed so as to maintain the ultraviolet radiation within the cavity. The sanitizer further includes an indicator strip located at a junction between the base and the cover, the indicator strip being at least partially translucent to ultraviolet radiation so as to appear illuminated when the cover is in the closed position and the ultraviolet radiation source is activated, and a cradle for supporting the portable electronic device within the cavity, the cradle being pivotable from a stowed position within the cavity to an exposed position away from the cavity. The sanitizer further includes a first sensor to detect whether or not the cover is in its closed position and a second sensor to detect the presence or absence of a portable electronic device within the cavity. A controller preferably activates the ultraviolet radiation source for a first predetermined period of time when the first sensor senses that the cavity is enclosed (e.g., cover is closed) and the second sensor senses the presence of a portable electronic device within the cavity. The controller may in addition to or alternately activate the ultraviolet radiation source based on a signal from a manual interface (such as a switch). The controller may also activate the ultraviolet light source for a second predetermined period of time when the second sensor detects the absence of a portable electronic device within the cavity so that the light source can decontaminate the cavity.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION

Reference will now be made in detail to various embodiments of the present invention, an example of which is illustrated in the accompanying drawings.

A sanitizer is provided having a cavity into which a portable electronic device fits, and a source of ultraviolet radiation with a wavelength and intensity suitable for the sanitization of a portable electronic device and positioned to irradiate the exterior of a portable electronic device fitted into the cavity of the sanitizer. The sanitizer has a cover that closes to substantially prevent the escape of ultraviolet radiation when the portable electronic device is fitted into the cavity of the sanitizer, and that is interlocked or otherwise interconnected (such as through one or more sensors and/or switches) to the source of ultraviolet radiation so that radiation is not generated unless the cover is closed. A mechanism may be provided to eject the portable electronic device or to make the portable electronic device readily accessible when the lid of the sanitizer is opened.

Figure 1:
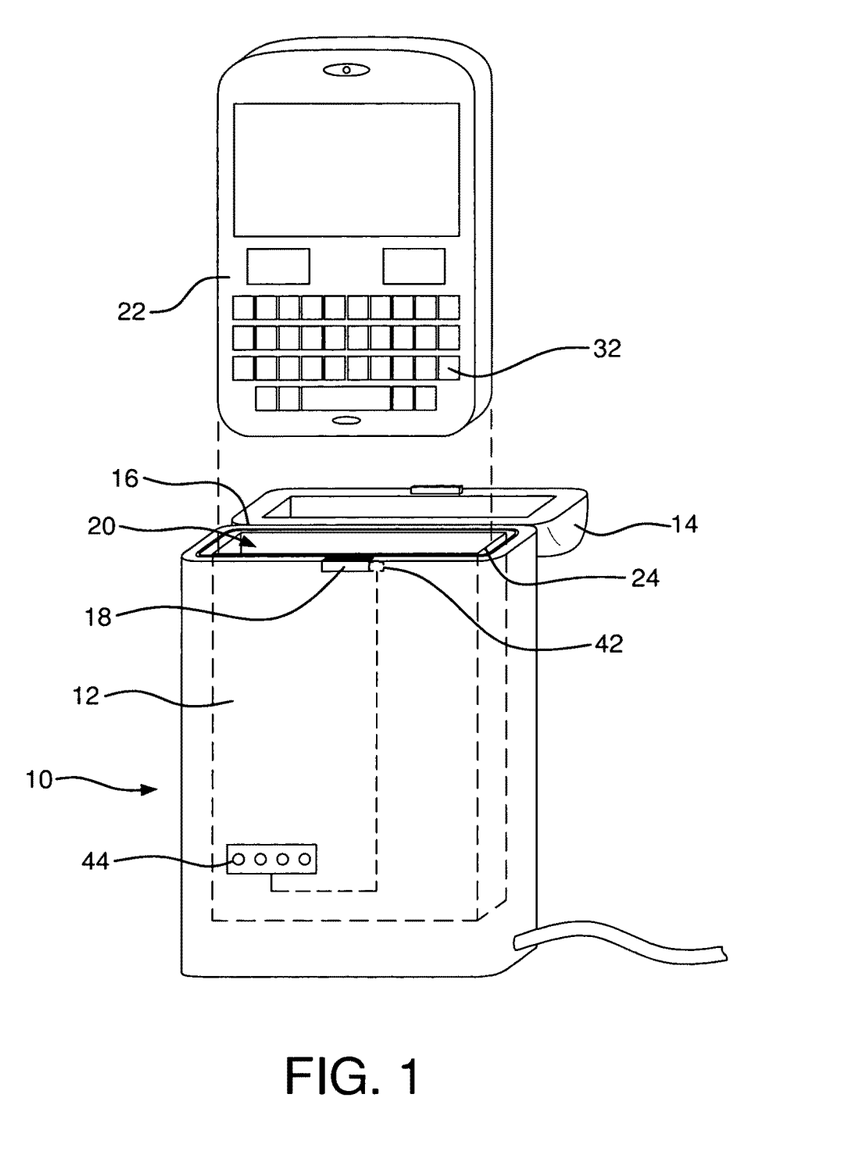
FIG. 1 is an external view of an embodiment of a sanitizer, and a portable electronic device prior to insertion in the sanitizer.
Figure 2:
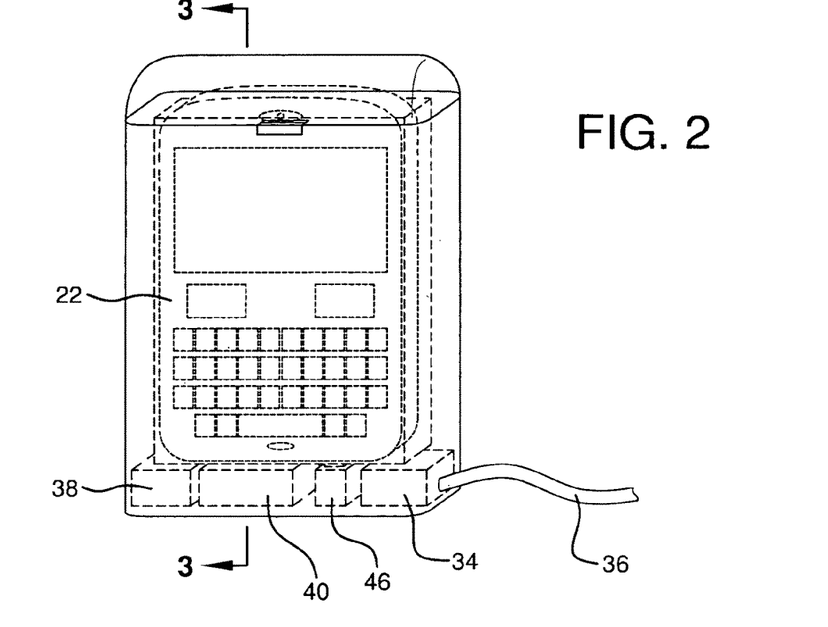
FIG. 2 is a phantom view showing the interior of the sanitizer of FIG. 1, wherein the portable electronic device is disposed inside the sanitizer.

Referring to FIGS. 1 and 2, one embodiment of a sanitizer 10 includes a body 12 and a cover 14. As depicted, the cover 14 is attached to the body 12 by hinges 16, and is provided with a catch or lock 18. Alternatively, the cover 14 can be removable from the body 12 and can be installed onto the body 12 by way of a friction fit, snap fit, or other reversible mechanical joint known in the art.

Figure 3:
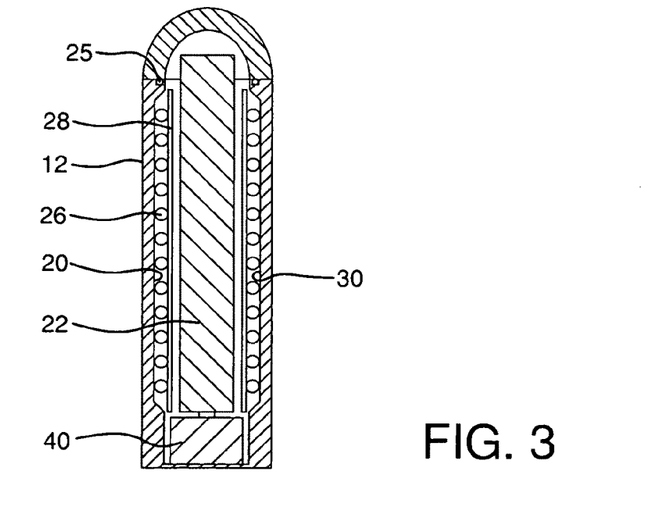
FIG. 3 is a cross-sectional view through the sanitizer and portable electronic device of FIG. 2, showing an arrangement of ultraviolet radiation sources in one embodiment.

The body 12 has an open interior cavity 20 formed by interior walls or sections of the body 12. The cavity 20 is shaped and dimensioned to receive a portable electronic device 22. In the embodiment shown in the FIGS. 1 and 2, the portable electronic device 24 may be a personal digital assistant (PDA) or cellular telephone equipped with user interface elements such as a display screen and a keypad 32. As shown in FIGS. 2 and 3, when the portable electronic device 22 is fully inserted into the cavity 20 of the body 12, the cover 14 can be closed onto the body 12 to substantially enclose the portable electronic device 22 within the cavity 20. A suitable light seal 24 can be provided at a junction where the body 12 and the cover 14 meet, so that when the cover 14 is closed onto the body 12, ultraviolet radiation from the cavity 20 cannot escape from the junction, or cannot escape at sufficient intensity to be hazardous. The seal 24 may include any suitable material which inhibits the passage of light, such as a rubber or felt gasket, or a close or overlying fit between the cover 14 and the body 12. The body 12 and the cover 14 are made of, or include a layer, lining, or coating of, a material that is substantially opaque to ultraviolet radiation.

Inside the body 12 is disposed one or more ultraviolet radiation sources 26 for emitting ultraviolet light. In one embodiment, an array of ultraviolet radiation light sources 26 is provided. In the embodiment shown in FIG. 3, the radiation sources 26 are fluorescent tubes. Alternatively, the radiation sources 26 can be discharge tubes, lasers, or light emitting diodes tuned to a particular frequency or range of frequencies. The ultraviolet radiation sources 26 may be located inside one or more recesses (not shown) formed in a wall of the body 12 and may be separated from the electronic device by an ultraviolet-transparent wall 28.

In order to position the electronic device within the cavity 20, rails or other guides may be incorporated either as separate components or formed into the body to position and guide the portable electronic device 22 into the body 12. The guides may be made of ultraviolet transparent material, and/or may be positioned to cover only parts of portable electronic device 22 that are at low risk for contamination. For example, the guide may be a seat formed in a wall of the body 12 and configured to engage only a small section of the portable electronic device.

The interior walls of the cavity 20 may include one or more reflectors 30, or the reflectors 30 can be disposed between the ultraviolet radiation sources 26 and the interior walls of the body 12, to increase the efficiency of use of the ultraviolet radiation, to control the distribution of the ultraviolet radiation about the cavity 20, and/or to maximize the exposure of all surfaces of the portable electronic device 22 to the ultraviolet radiation.

In one embodiment, the opaque layer itself is a reflective lining on the interior walls the body 12 and cover 14 to reflect the emitted ultraviolet radiation in order to thoroughly irradiate the portable electronic device 22. Alternatively, or in addition, lenses may be provided between the radiation sources 26 or reflectors 30 and the cavity 20 of the sanitizing device 10 to enhance the irradiation provided by the radiation sources 26. Lenses or reflectors 30 may not be required, depending on the light distribution from the sources 26. For example, in one embodiment, many light emitting diodes (LEDs) are mounted on a flat, opaque substrate so that they emit radiation into only one hemisphere, and are encapsulated in a refractive dome that further directs the radiation in an outward direction. Suitably selected LEDs may thus produce a satisfactory distribution of radiation without further optical aids. In generally, any suitable ultraviolet radiation source may be used, including without limitation fluorescent lamps or tubes, incandescent bulbs, discharge lamps, lasers, or LEDs. From an engineering point of view, an array of LEDs provides the advantages of small size, robustness, and efficiency. However, from a cost perspective a fluorescent lamp provides the advantages of wide availability and low cost.

Commonly, the portable electronic device 22 has a keypad 32 with projecting keys. Because the keys of the keypad 32 provide sheltered recesses in which grime and contaminants may accumulate, the ultraviolet radiation sources 26 and/or the reflectors 30 may be arranged to provide particularly thorough irradiation of the keypad 32, including oblique rays from various sides and angles.

The cavity 20 of the sanitizer 10 can act as a docking station for a portable electronic device 22 inserted thereinto, providing an electrical connection for recharging of a battery in the portable electronic device 22 and/or a data connection for synchronizing the portable electronic device 22 with another data store, a wireless or a wired service, to permit access to and/or control of the portable electronic device 22 from outside the sanitizer 10, or other purposes. As shown in FIG. 3, a power pack 34 is disposed in one end of the sanitizer 10. The power pack 34 receives utility power from a flexible cable 36. The power pack 34 provides power to the ultraviolet radiation sources 26 under control of a control unit 38. Additionally, the power pack 34 may provide power to a docking connector 40 via a cable 36. The docking connector 40 is adapted to connect to the portable electronic device 22 when the portable electronic device 22 is disposed within the cavity 20. The cable 36 and the connector 40 can provide power for recharging the portable electronic device 22. In addition, or alternatively, the cable 36 and connector 40 can provide a data connection between the portable electronic device 22 and the outside world. As non-limiting examples, the data connection can include an Ethernet connection, a USB or mini-USB connection, or the like. The connector 40 may be omitted, especially if the sanitizer 10 is to be used only with a portable electronic device that does not have a power or data connector configured to be capable of interconnecting with the docking connector 40, or if the sanitizer 10 is to be used with a wide variety of different portable electronic devices that have incompatible connectors.

The sanitizing device 10 can include a switch 42 in the catch 18 that is connected to the control unit 38 to enable the control unit to detect that the cover 14 has been closed on the body 12 to enclose a portable electronic device 22 within the cavity 20. Alternatively, a sensor may be activated upon closing the cover 14. The sensor can include, but is not limited to, one or more of a depression switch, electrical contacts, and an optical sensor. In one embodiment, the control unit 38 comprises a contact on the body 12 and a mating contact on the cover 14, the contacts completing a circuit to activate the ultraviolet radiation source only when the cover 14 is in the closed position to enclose the cavity 20.

In operation of the embodiment of the sanitizing device 10 shown in FIGS. 1 through 3, a user places a portable electronic device 22 into the cavity 20 of the body 12, and closes the cover 14 to enclose the portable electronic device 22 within the cavity 20. The control unit 38 may detect that cover 14 is securely closed, for example, by way of the switch 42 in the catch 18 or a sensor or depression switch that is activated upon closing of the lid. The control unit 38 may also detect that the portable electronic device 22 is present, for example, by a mechanical switch operated by weight or presence of the portable electronic device 22, by a light beam occluded by the portable electronic device 22, or in some other way. If the sanitizer 10 is to be used with a portable electronic device 22 that docks with the connector 40, then the control unit 38 may be configured to detect signals, such as power current, passing between the portable electronic device 22 and the connector 40 as portable electronic device 22 recharges its battery. It is also contemplated that the control unit 38 may be activated by a manual interface such as a switch mounted external to the sanitizer 10.

Upon sensing the presence of a portable electronic device 22 in the cavity 20, or upon manual activation, the control unit 38 activates the ultraviolet radiation sources 26 to sanitize the portable electronic device 22. The control unit 38 can include a timer, such that after a programmed time sufficient to achieve a desired level of sanitization, the control unit 38 deactivates the ultraviolet radiation sources 26. If the switch 42 detects an attempt to release the catch 18 and/or open the cover 14 while the ultraviolet radiation sources are activated, the control unit 38 immediately shuts off power to the ultraviolet radiation sources 26. If the cover 14 is closed with no portable electronic device 22 inside the cavity 20, the control unit 38 may be configured to activate the ultraviolet radiation sources 26 to sanitize the cavity 20, if desired.

One or more indicator lamps 44 may be provided on the outside of the body 12, to indicate the status of the sanitizer 10 and/or the portable electronic device 22, for example, to show whether sanitization using the ultraviolet radiation sources 26 is proceeding or has been completed, whether the battery of the portable electronic device 22 is charging or is fully charged, and so on.

An ejector 46 may be mounted in the cavity 20 of the body 12 to lift the portable electronic device 22 to a position at which it can easily be grasped by the user and removed from the cavity 20 when the cover 14 is opened. The ejector 46 may include a lever operated through linkages by opening the cover 14. The ejector 46 may also include a spring that is compressed when the portable electronic device 22 is pushed down into the cavity 20 such that the spring constantly urges the portable electronic device 22 upwards. When in the cavity 20, the portable electronic device 22 may be held down by the cover 14 or the spring may be held by a sear. The sear may be released by raising the cover 14 or by releasing the catch 18, or by completion of sanitization. Other arrangements may be used, as is well known in the art.

Figure 4:
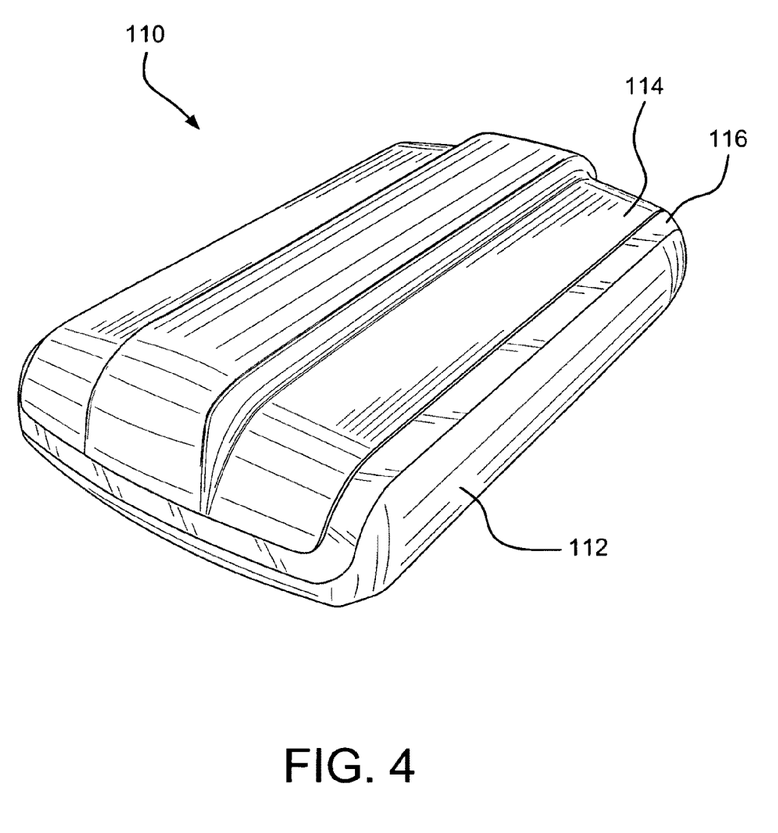
FIG. 4 is a perspective view showing the exterior of another embodiment of a sanitizer.
Figure 5:
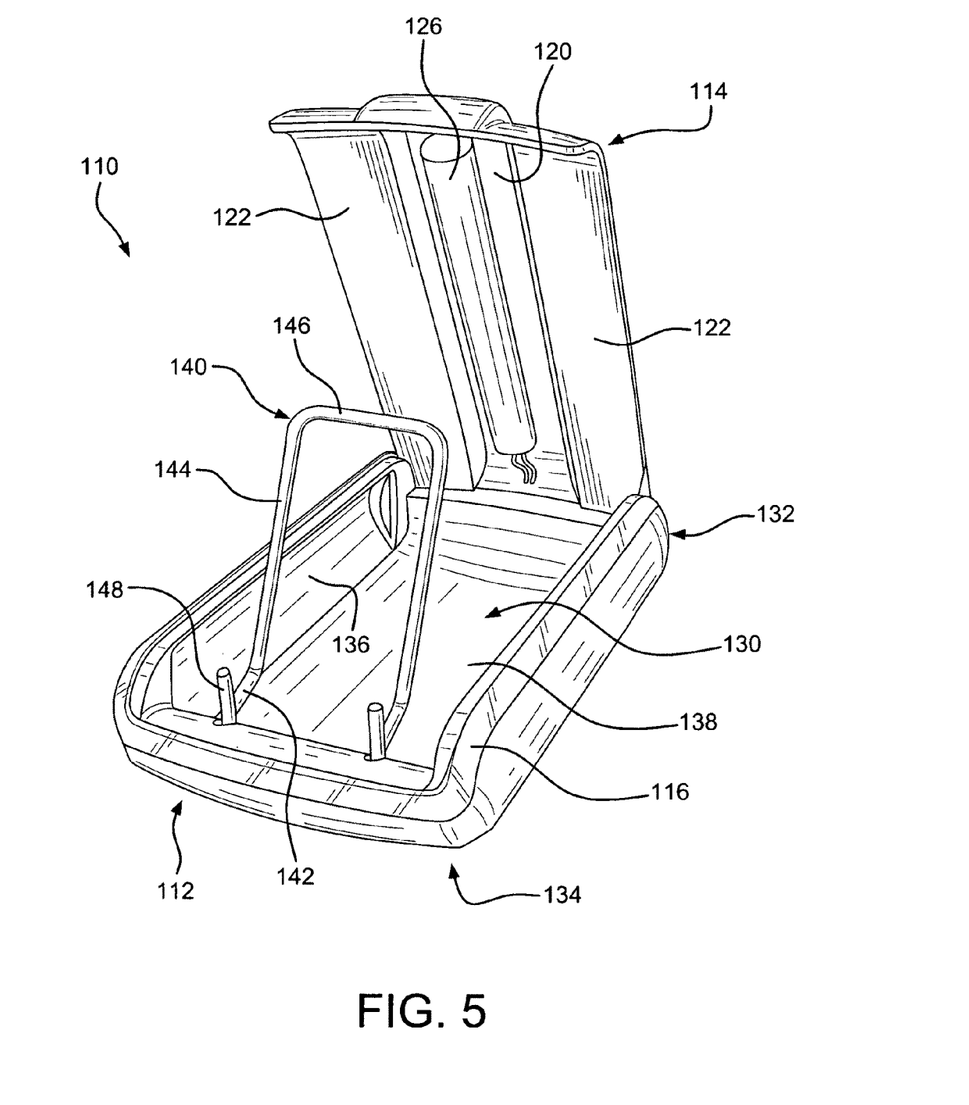
FIG. 5 is a perspective view showing the interior of the sanitizer of FIG. 4.

Referring to FIGS. 4 through 7D, another embodiment of a sanitizing device or sanitizer 10 is disclosed. FIG. 4 shows the exterior of the sanitizing device 110 in a closed configuration, and FIG. 5 shows the exterior and interior of the sanitizing device 110 in an open configuration. In describing the sanitizing device 100, a vertical frame of reference is used wherein the sanitizer 110 has a downward facing bottom and an upward facing top, such that in use the base 112 will generally be supported by a horizontal surface and the cover 114 will open upwardly away from the base 112. However, it is understood that the sanitizer 110 can be devised to function equally well in orientations differing from the described vertical frame of reference.

As depicted, the sanitizing device 110 includes a base 112 having an interior cavity 130 opening onto a side of the base 112, and a cover 114 for covering the opening in the base 112 to enclose the cavity 130. The base 112 can further include a strip of material 116 that is translucent or partially transparent when exposed to ultraviolet radiation, so that it is possible when the cover 114 is closed to visibly detect from outside the sanitizing device 110 that ultraviolet radiation is present in the cavity 130. The cover 114 is hingedly connected to the base 112 such that the cover 114 opens in a pivoting motion about a first end 132 of the base 112, enabling a portable electronic device to be inserted into the cavity 130 via an opposite second end 134 of the base 112.

A cradle 140 can be provided for supporting a portable electronic device or other device to be sanitized. The cradle 140 is pivotably mounted to the base 112 at or near the second end 134 of the base 112, to provide support for the portable electronic device both when the device 110 is open, such that the portable electronic device is accessible, and when the device 110 is closed, such that the portable electronic device is positioned within the cavity 130. As shown in FIG. 5, the cradle can be made from rails, including a pair of front stub rails 148 each extending upward from a pair bottom rails 142, each bottom rail 142 being adjoined at a bent junction to a rear rail 144, the two rear rails 144 being joined together by a top rail 146. The front stub rails 148 are oriented generally vertically and the bottom rails 142 are oriented generally horizontally and extend from the front stub rails 148 in the direction from the second end 134 toward the first end 132. The rear rails 144 extend upwardly and rearwardly from the bottom rails 142. Thus, the rails provide a seat for the portable electronic device.

When the sanitizer 110 is open and a portable electronic device is received in the cradle 140, the weight of the electronic device is generally supported by the bottom rails 142 and the electronic device is enabled to lean rearwardly onto the rear rails 144 and is prevented from sliding out of the cradle 140 by the front stub rails 148. Accordingly, the portable electronic device can be readily placed into or removed from the cradle 140. As the sanitizer 110 is transitioned from the open configuration to the closed configuration, the cradle 140 pivots while supporting and guiding the portable electronic device until the portable electronic device is disposed generally horizontally within the cavity 130 and the cover 114 has enclosed the cavity 130.

Figure 9:
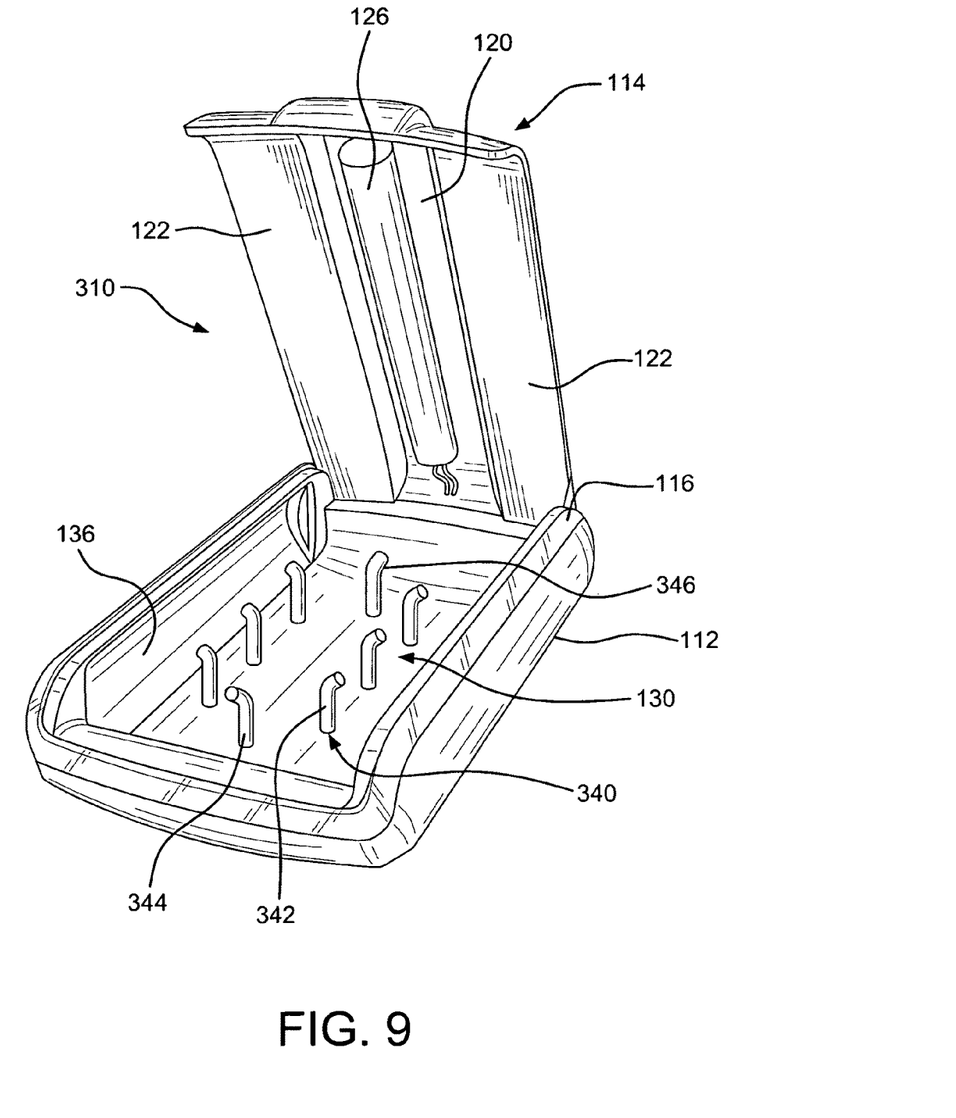
FIG. 9 is a perspective view showing the interior of another embodiment of the sanitizer of FIG. 4.

Alternatively, as shown in FIG. 9, a cradle 340 can be provided comprising a plurality of posts extending vertically upward from the body 112 into the cavity 130. For example, the cradle can include side posts 342, one or more front posts 344, and one or more rear posts 346. As depicted, each post includes a slanted surface to encourage the portable electronic device to be generally centered within the cavity 130.

As depicted in FIG. 5, the sanitizer 110 includes an ultraviolet radiation source 126 disposed in the cover 114. The ultraviolet radiation source 126 is capable of emitting ultraviolet light in the range of about 200 nm to about 300 nm. In one embodiment, the ultraviolet radiation source 126 is capable emitting ultraviolet light at about 254 nm. The ultraviolet radiation source 126 can be located within a recess 120 in the cover 114. The surface of the recess 120, as well as an inner surface 122 of the cover 114 can be reflective, or coated with a reflective material such as a metalized material, to aid in the uniform dispersion of ultraviolet light throughout the cavity 130. Power can be supplied to the ultraviolet radiation source 126 by a power supply, transformer, or other like conventional means known in the art.

In the base 112, the cavity 130 is defined by a bottom wall 138 and side walls 136 which are shaped to receive a portable electronic device. The surfaces of the bottom wall 138, as well as the surfaces of the side walls 136, can be reflective, or coated with a reflective material such as a metalized material, to aid in the uniform dispersion of ultraviolet light throughout the cavity 130. When the cover 114 is closed, the cradle 140 supports the portable electronic device within the cavity 130 so that the rails 144 and 146 of the cradle, and thus the back side of the portable electronic device that is support by the rails 144 and 146, are spaced apart from the bottom wall 138 to allow the ultraviolet radiation to access the back side of the portable electronic device, and the front side of the portable electronic device opposite the back side is spaced apart from the inner surface 122 of the cover 114. Similarly, the cradle 140 supports the portable electronic device such that the sides of the portable electronic device, which are adjacent to the side walls 136 of the cavity 130, are spaced apart from the side walls 136 to allow ultraviolet radiation to access the sides of the portable electronic device. Accordingly, ultraviolet radiation emitted by the light source 126 can directly, or indirectly by way of reflection off of the reflective surfaces 120, 122, 136, and 138, access all portions of the portable electronic device.

In one embodiment, the material of construction of the cradle 140 is transparent to ultraviolet radiation so that a sufficient amount of ultraviolet radiation can penetrate the rails 142, 144, 146, 148 to irradiate the portions of the portable electronic device disposed thereunder. In another embodiment, the cradle 140 is configured so as to minimize the contact area between the cradle rails and the portable electronic device so that substantially all of the portable electronic device is exposed to the ultraviolet radiation.

As shown in FIGS. 4 and 5, the sanitizer 110 may include an indicator strip 116 composed of material that is translucent to visible light that is produced by the ultraviolet radiation. Suitable materials would be certain plastics that absorb ultraviolet light while permitting visible light to as through. The indicator strip 116 can be located adjacent to at least a portion of the junction between the base 112 and the cover 114 so that when the cover 114 is closed and the ultraviolet radiation source 126 is activated, the indicator strip 116 glows or appears illuminated to provide a visual indication that the sanitizer 110 is operating. In one embodiment, the indicator strip 116 is composed of a translucent blue material and extends along substantially the entire junction between the base 112 and the cover 114.

Instead of an indicator strip, it is also contemplated that the sanitizer may include an indicator located on the sanitizer and which can be activated by the controller when the cover is in the closed position and the ultraviolet radiation source is on so as to provide a visual indication that the sanitizer is on. In one embodiment, the indicator may be an LED. The LED may be pulsed by the controller during activation of the ultraviolet light source.

Figure 8:
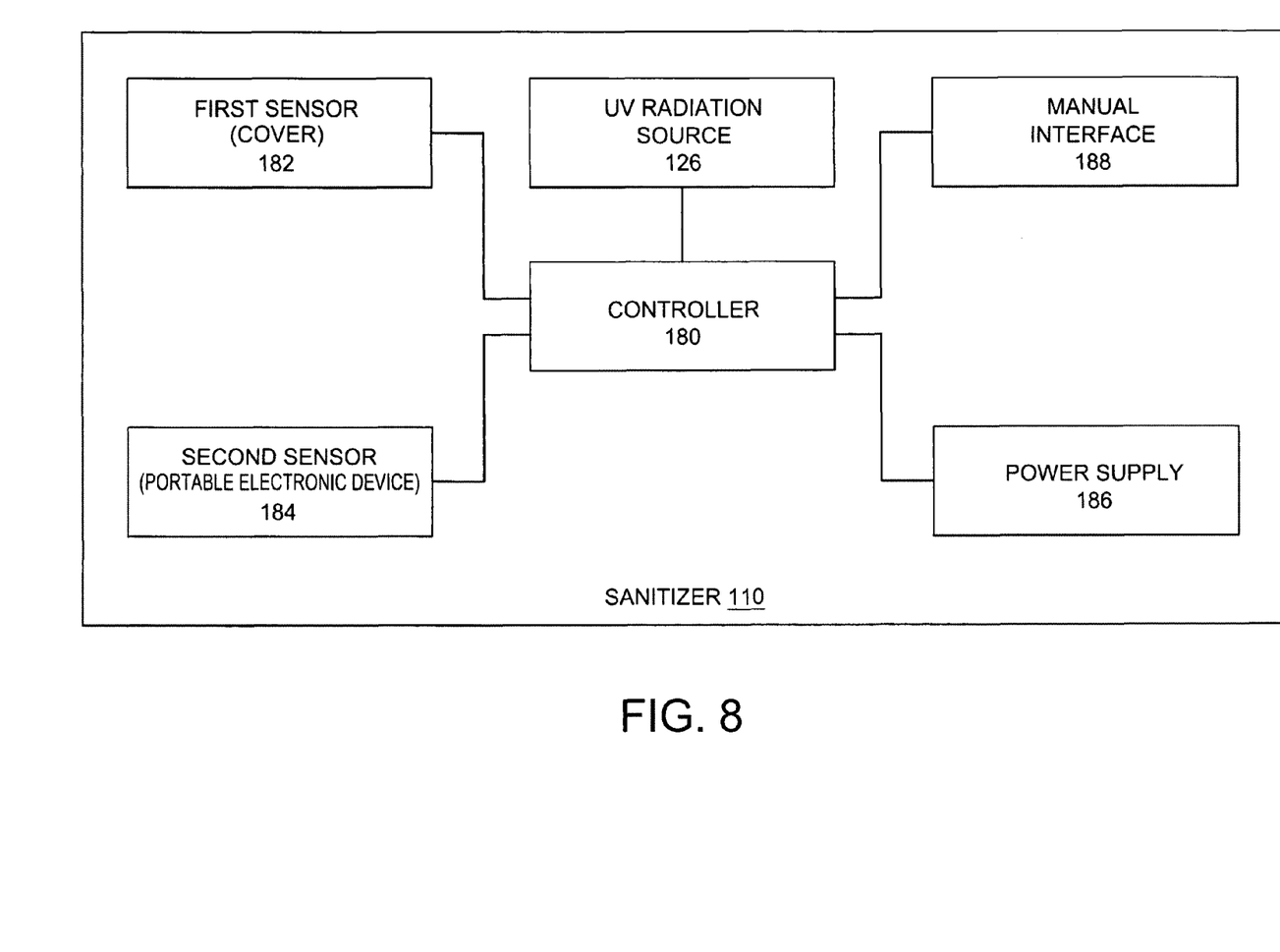
FIG. 8 is a control system schematic for operating a sanitizer.

As shown in FIG. 8, the sanitizer 110 includes a controller 140 for controlling operation of the sanitizer 110 and a power supply 186 for providing power to the controller 180 and to the ultraviolet radiation source 126. The controller 180 can control operation of the sanitizer 110 in several circumstances, including but not limited to when the cavity 130 is empty (i.e., no portable electronic device is present), when the cover 114 is open, and when the cavity 130 contains a portable electronic device. In one embodiment, the controller 110 is configured to detect whether the cover 114 is open or closed and to control operation of the sanitizer 110 accordingly. For example, the ultraviolet radiation source 126 is disabled from emitting ultraviolet light when the cover 114 is open and is enabled to emit ultraviolet light when the cover 114 is closed. A first sensor 182 senses or detects whether the cover 114 is open or closed with respect to the base 112. The first sensor 182 can comprise a depression switch, an optical sensor, electrical contacts, or other sensor known in the art for determining the relative positions of the cover 114 and the base 112. In one embodiment, the first sensor 182 includes a contact on the base 112 and a mating contact on the cover 114, the contacts completing a circuit to activate the ultraviolet radiation source only when the cover 114 is in the closed position to enclose the cavity 130.

Similarly, in another embodiment, the controller 180 is coupled to a second sensor 184 to sense or detect the presence or absence of a portable electronic device within the cavity 130 and to control operation of the sanitizer 110 accordingly. For example, if the presence a portable electronic device is detected, the controller 180 can energize the ultraviolet radiation source 126 for a predetermined period of time determined to be sufficient for sanitization. The predetermined period of time may vary depending on the strength of the UV light source. In one embodiment of the sanitizer 110 using a 4 watt compact fluorescent tube, it is estimated that between 10 and 30 seconds would be sufficient to eliminate most bacteria present on a handheld device. If the absence of a portable electronic device is detected, the controller 180 can disable or not activate the ultraviolet radiation source 126. Optionally, the controller may track the amount of time elapsed since the ultraviolet radiation source 126 has been activated to sanitize the cavity 130 and may activate the ultraviolet radiation source 126 for a period of time in order to sanitize the interior surfaces of the base 112 and cover 114. The second sensor 184 may comprise a weight sensor, a depression switch, an optical sensor, or other sensor known in the art.

As discussed above, the sanitizer may include an manual switch or interface 188 located outside of the sanitizer 110 that a user can select to manually activate the sanitizer.

Figure 6A:
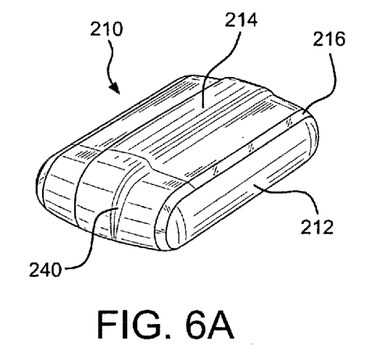
FIGS. 6A through 6E are perspective views showing the operation of an embodiment of a sanitizer moving from a closed position in which a cradle is retracted into the interior of the sanitizer to a position in which the cradle is exposed for receiving or delivering a portable electronic device.
Figure 6B:
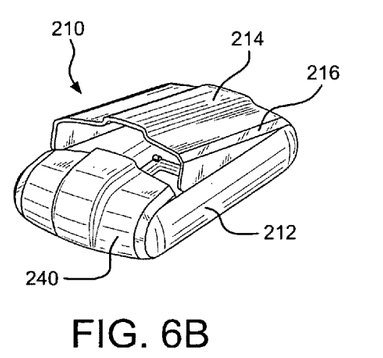
Figure 6C:
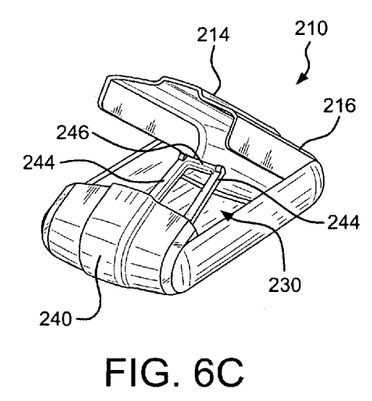
Figure 6D:
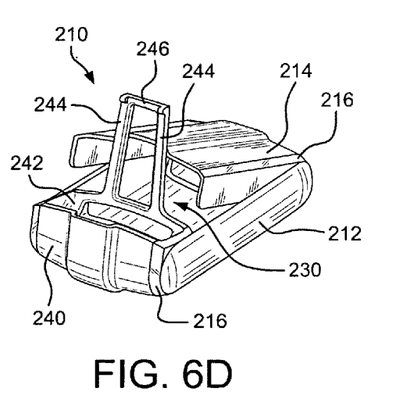
Figure 6E:
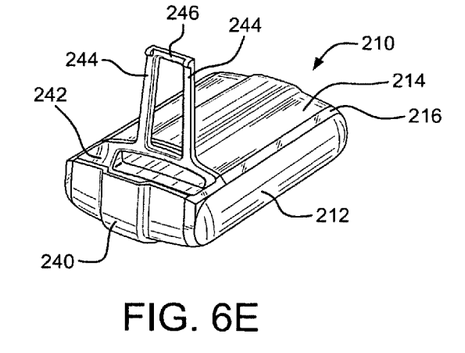
Figure 7A:
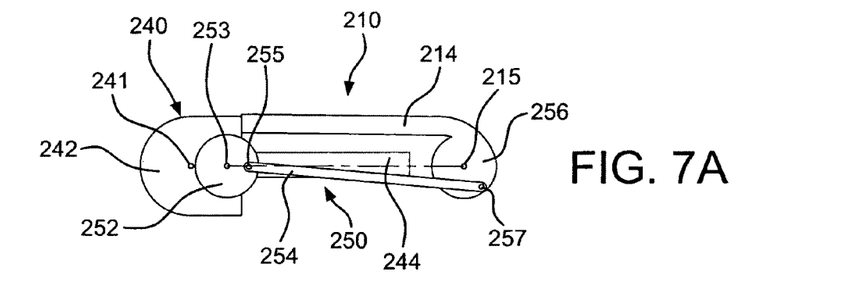
FIGS. 7A through 7D are schematic views showing the operation of an embodiment of a sanitizer moving from the closed to the open position.
Figure 7B:
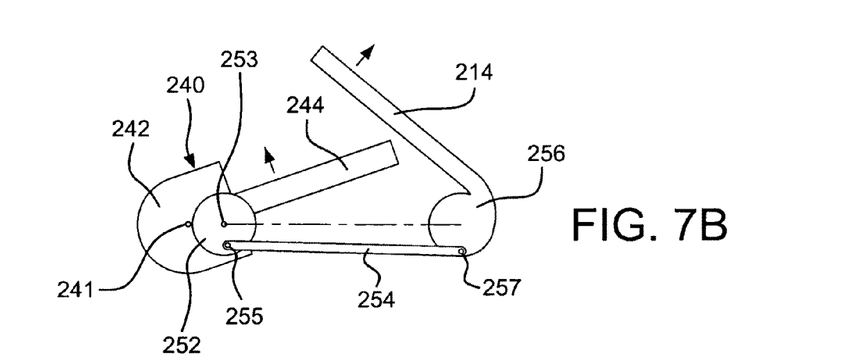
Figure 7C:
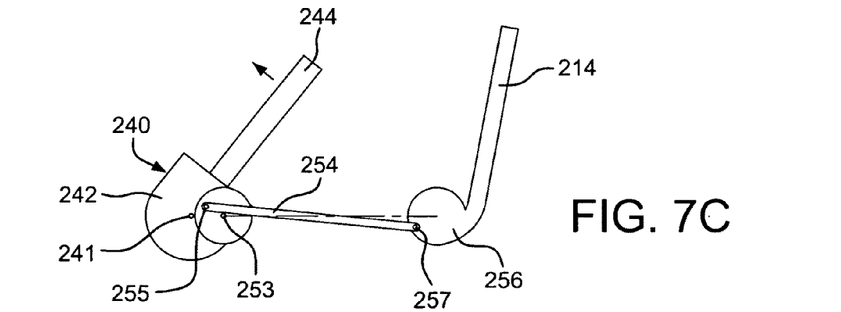
Figure 7D:
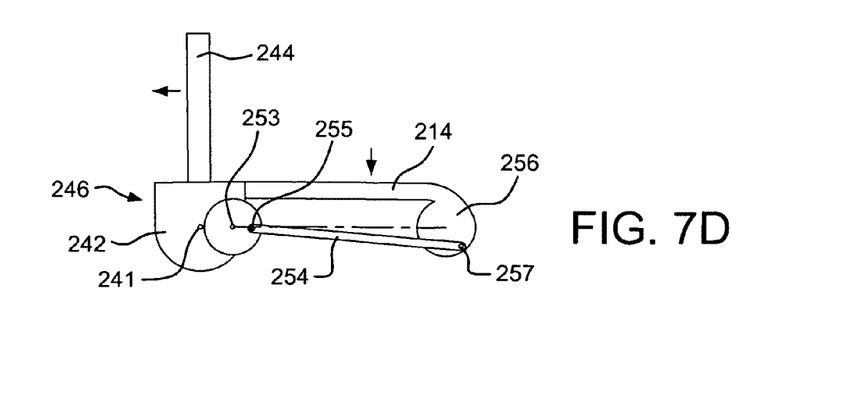

Another embodiment of a sanitizer 210 is depicted in FIGS. 6A through 7D. FIGS. 6A through 6E are perspective views showing successive steps in the opening of the sanitizer 210. The sanitizer 210 can be opened by a push-to-open latch as is known in the art, wherein pressure is applied and then released from the cover 214, and the cover 214 then pivots upward and rearward with respect to the base 212. The movement of the cover 214 can be driven by a coil spring, a motor, or other similar mechanism. FIG. 6A shows the sanitizer 210 in a closed configuration. FIG. 6B shows the sanitizer 210 after the cover 214 has released from the base 212 and is beginning to open. FIG. 6C shows that as the cover 214 begins to open further with respect to the base 212, a cradle 240 also begins to pivot upward and frontward with respect to the base 212. After the cover 214 has reached an amount of opening sufficient to allow the cradle 240 to pass, the cradle 240 continues to pivot upward and frontward with respect to the base 212 while the cover 214 preferably reverses direction and begins to pivot downward and frontward with respect to the base 212, as shown in FIG. 6D. As shown particularly in FIG. 6D, the cradle 240 includes a base seat 242 for receiving a bottom portion of a portable electronic device and back rails 244 and a cross rail 246 for supporting the back side of the portable electronic device. Finally, as shown in FIG. 6E, the cover 214 pivots to a fully closed position and the cradle 240 remains in a fully open position for receiving or delivering a portable electronic device from or to a user, respectively. By applying pressure to and then releasing the pressure from the cover 214, a reverse operation occurs until the cradle 240 is again stowed within the cavity 230.

A schematic of the operation of the sanitizer 210 of FIGS. 6A through 6E is shown in cross-sectional side view in FIGS. 7A through 7D, which show an actuating mechanism 250 for moving the cover 214 and the cradle 240 between the open and closed positions. The actuating mechanism 250 can be disposed internally to the sanitizer 210, or can be disposed externally to the sanitizer 210 but protected by a separate cover or the like. The actuating mechanism 250 includes a crank wheel 252 connected by a pivot pin 255 to one end of a link arm 254, the other end of the link arm 254 being connected by a pivot pin 257 to an eccentric bottom portion 256 of the cover 214. The crank wheel 252 can be driven by a coil spring, a motor, or other mechanism capable of providing rotational motion to the crank wheel 252.

Gearing (not shown) connects the crank wheel 252 to the cradle 240 in a ratio of approximately 4:1, so that as the crank wheel 252 rotates by an angle of about 360° with respect to its axis 253, the cradle 240 is driven via the gearing to rotate by an angle of about 90° with respect to its axis 241. Thus, in approximately one full rotation of the crank wheel 252, the cradle 240 is pivoted from a closed position to an open position, and in approximately one full rotation of the crank wheel 252 in the opposite rotational direction, the cradle 240 is pivoted from an open position to a closed position.

The pivot pin 255 is eccentrically located on the crank wheel 252 (i.e., the pivot pin 255 is offset from the axis of rotation 253 of the crank wheel 252 so that as the crank wheel 252 rotates, the link arm 254 is driven in a generally reciprocating motion. Similarly, the pivot pin 257 is eccentrically located on the bottom portion 256 of the cover 216 (i.e., the pivot pin 257 is offset from the axis of rotation 215 of the cover 214) so that the reciprocating motion of the link arm 254 causes a pivoting motion of the cover 214 about its axis 215. The operation of the actuating mechanism 250 can be described as a four bar linkage of a type well known in the art, wherein a first bar is defined by the base 212 to maintain the axis 253 of the crank wheel 252 and the axis 215 of the cover 214 fixed with respect to each other, a second bar is defined by the crank wheel 252 as the distance between the axis 253 and the pivot pin 255, a third bar is defined by the eccentric bottom portion 256 of the cover 214 as the distance between the axis 215 and the pivot pin 257, and a fourth bar is defined by the link arm 254 as the distance between the pivot pin 255 and the pivot pin 257. The ratio of the lengths of the second bar (the distance between the axis 253 and the pivot pin 255) and the third bar (the distance between the axis 215 and the pivot pin 257) is set to be less than 1:1 such that while the crank wheel 252 makes a full rotation, the cover is caused to rock back and forth over a range of about 90°. In particular, a 0° position of the crank wheel 252 can be defined by the cover 214 being in a closed position. As the crank wheel 252 rotates to approximately halfway (i.e., between about 160° and about 200°), the cover 214 pivots to a fully open position (i.e., about 90° from the cover closed position), and as the crank wheel 252 rotates from approximately halfway to a full rotation (i.e., about 360°), the cover 214 pivots back to a fully closed position.

It is also contemplated that the cover 214 and cradle 240 may be interconnected, such as through a linkage, such that, when the cradle 240 is in its exposed or upright position and the cover 212 is open, pushing on the cover 212 would automatically, through the linkage, cause the cradle 240 to rotate or pivot into its stowed position. It is also contemplated that a spring may be used to bias the cradle 240 into its upright position and to bias the cover 214 into its open position.

A sanitizer as disclose herein can be designed to accommodate a specific portable electronic device, wherein the interior of the sanitizer is shaped and sized to receive the portable electronic device snugly and securely, and the radiation source, including any reflectors, is arranged to irradiate the exterior surfaces of the portable electronic device in an optimal manner. Alternatively, a sanitizer can be designed to accept several generally similar types of portable electronic devices, particularly for cases in which numerous makes and models of portable electronic devices of approximately the same shape and size are available; while it may be impractical to have a differently sized and shaped sanitizer for every slightly different portable electronic device, it may be feasible to have a small number of sizes and shapes of sanitizers to accommodate ranges or types of portable electronic devices. As a non-limiting example, most "flip" or "clamshell" type cellular telephones are substantially similar in shape and size, as are "full keyboard" type devices used for texting and e-mailing applications.

While the present invention has been illustrated in FIGS. 4-9 with the ultraviolet light source in the cover, it is also contemplated that the light source could be located in the base with an intermediate surface that forms a bed on which the electronic device can be placed, the intermediate surface being at least partially transparent to ultraviolet radiation. For example, the intermediate surface may be made from glass or plastic or other similar material.

As with the first embodiment, the power source on the sanitizer in FIGS. 4-9 may be configured to connect to the personal electronic device to power (charge) the device while stored. Alternately, an aperture with a suitable seal, may be formed in the housing which permits the device's existing power cord to extend out of the housing.

Figure 10A:
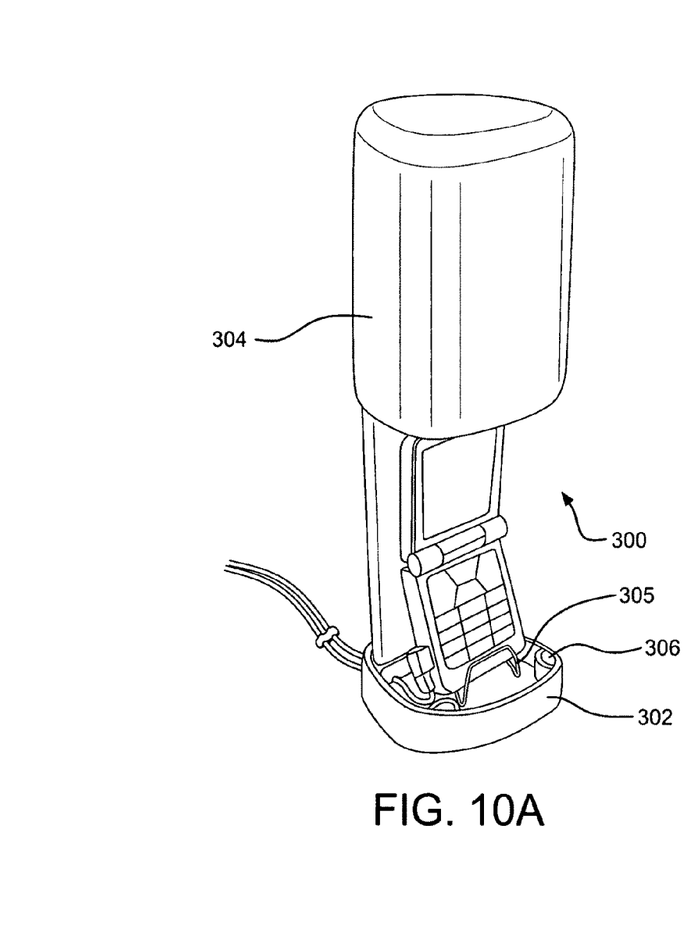
FIGS. 10A and 10B illustrate an alternate embodiment of the sanitizer with a sliding cover
Figure 10B:
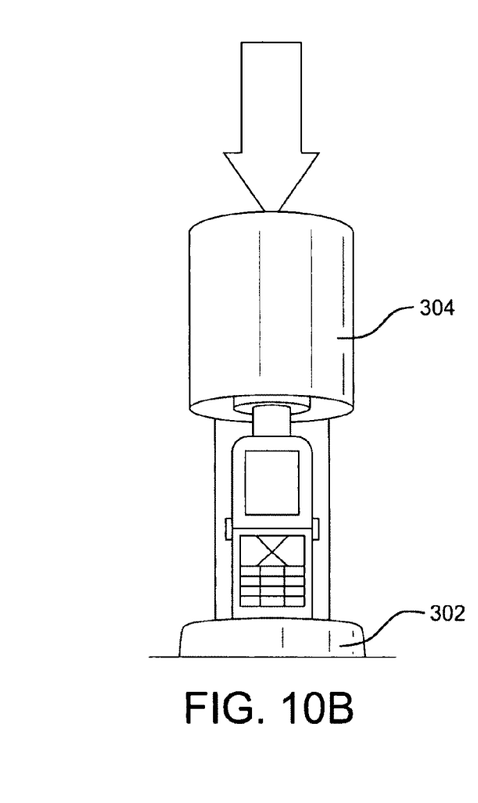

Referring now to FIGS. 10A and 10B, an alternate embodiment of the sanitizer are shown. The sanitizer 300 includes a base 302 and a cover 304. The cover is attached to the base so that is can slide upward to reveal the cradle 305 for holding the electronic device. The ultraviolet light source may be located in the base or more preferably the cover. When the cover is slid downward, a contact on the cover connects with a contact 306 on the base to complete the circuit. A controller controls activation of the light source. Upon completion of the sanitizing, the unit can be configured to automatically release the cover allowing it to slide upward.

Figure 11A:
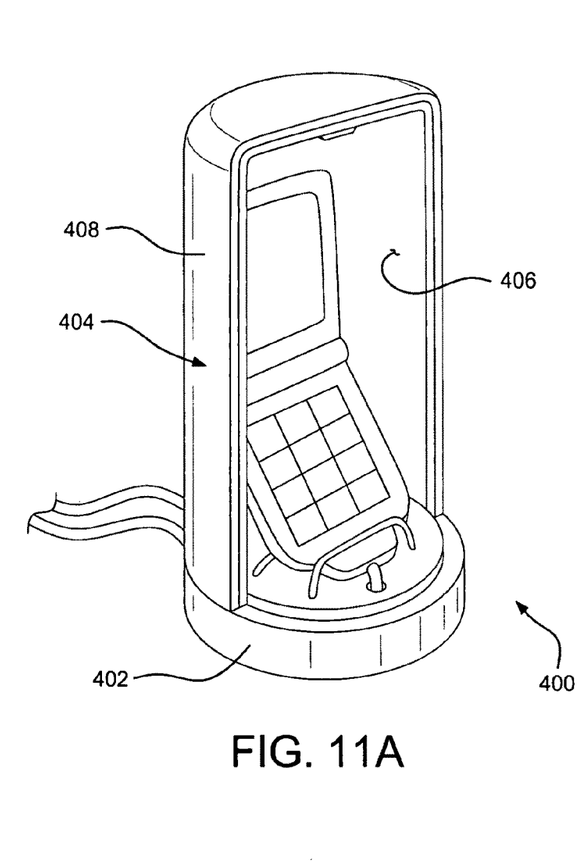
FIGS. 11A and 11B illustrate another alternate embodiment of the sanitizer with a cover that includes a rotatable cover section.
Figure 11B:
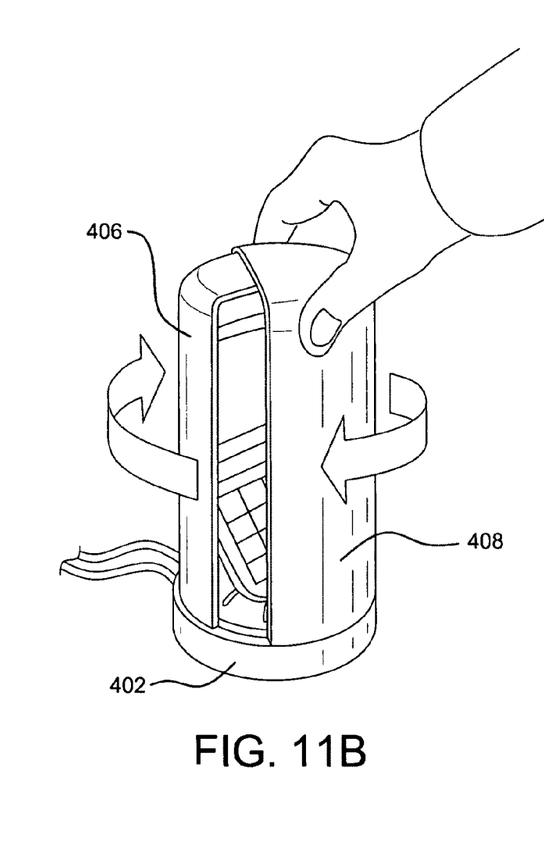

FIGS. 11A and 11B show another embodiment of the sanitizer 400 with a base 402 and a cover 404. The cover 404 includes a fixed rear cover section 406 and a rotatable front section 408. A cradle is mounted to the base. In use, the user can either swing the front cover section closed or may press a button to cause the front cover portion to rotate into a closed position enclosing the electronic device. See FIG. 11B. When the cover is closed, the controller can activate the ultraviolet light sources the sanitize the electronic device.

Figure 12:
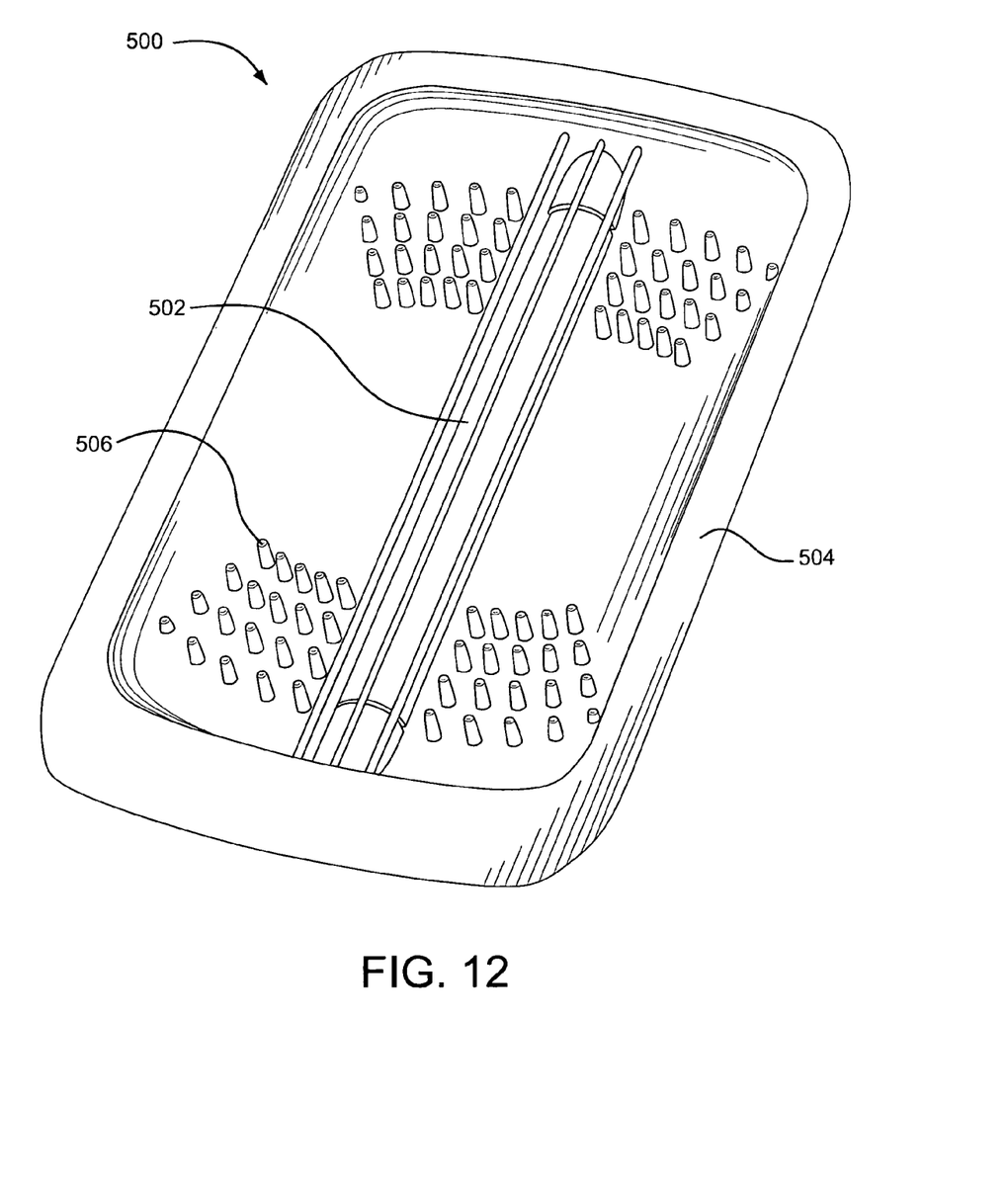
FIG. 12 illustrate another embodiment with the support for holding the electronic device being a plurality of upwardly protruding ribs

FIG. 12 illustrates the bottom or base of another embodiment of the invention 500. In this embodiment, the light source 502 is mounted on the base 504. A plurality of raised projections or supports 506 project upward beyond the top of the light source so as to provide clearance. During use, the electronic device is placed onto the projections, preferably face down, and the cover (not shown) is closed. When the light source is activated, the light illuminates the part of the electronic device resting on the projections. The clearance between the light source and the tops of the projections provides a high range of illumination and allows the UV light to pass beyond the electronic device and reflect off the side walls to irradiate the opposite side of the electronic device. While projections are shown in the figure, the supports can be a series of ribs. The projections can be made from various materials including plastic or rubber, and are preferably designed to provide some cushioning for the device.

Various modifications and variations can be made in the present invention without departing from the spirit or scope of the invention. Thus, it is intended that the present invention cover the modifications and variations of this invention provided they come within the scope of the appended claims and their equivalents.

The invention claimed is:

1. A sanitizer for sanitizing a portable electronic device, the sanitizer comprising:
 a base including a cavity for receiving the electronic device;
 at least one ultraviolet radiation source in the cavity for emitting ultraviolet radiation into the cavity;
 a cover cooperating with the base, the cover moving between an open position wherein the electronic device can be inserted into or removed from the cavity and a closed position wherein the cavity is enclosed so as to substantially maintain the ultraviolet radiation within the cavity;
 a controller for enabling the ultraviolet radiation source to be activated only when the cavity is enclosed; and
 a plurality of raised projections in the cavity projecting upward beyond the top of the light source to support the electronic device when placed in the cavity.

2. The sanitizer of claim 1, wherein the ultraviolet radiation source includes at least one of a fluorescent tube, a discharge lamp, a laser, and one or more light emitting diodes.

3. The sanitizer of claim 1, wherein at least a portion of the cavity and a portion of the cover are lined with a reflective surface.

4. The sanitizer of claim 1, the controller comprising a contact on the base and a mating contact on the cover, the contacts completing a circuit to activate the ultraviolet radiation source when the cover is in the closed position.

5. The sanitizer of claim 1, the controller interfacing with a first sensor to determine whether or not the cover is in a closed position.

6. The sanitizer of claim 5, the controller further interfacing with a second sensor to determine the presence or absence of a portable electronic device within the cavity.

7. The sanitizer of claim 6, wherein the controller activates the ultraviolet radiation source for a first predetermined period of time when a portable electronic device is present within the cavity.

8. The sanitizer of claim 6, further comprising a manual switch, wherein the controller activates the ultraviolet radiation source based on a signal from the manual switch for a second predetermined period of time when a portable electronic device is absent within the cavity.

9. The sanitizer of claim 6, wherein the controller periodically activates the ultraviolet radiation source for a second predetermined period of time when a portable electronic device is absent within the cavity.

10. The sanitizer of claim 9, wherein the periodic activation is based on an elapsed time since a previous activation of the ultraviolet radiation source.

11. The sanitizer of claim 1, further comprising a manual switch, wherein the controller activates the ultraviolet radiation source for a predetermined period of time based on a signal from the manual switch.

12. The sanitizer of claim 1, further comprising a cradle mounted to the base or the cover for supporting the portable electronic device.

13. The sanitizer of claim 12, wherein the cradle is mounted to the base and comprise the raised projections, the cradle configured to enable radiation emitted by the ultraviolet radiation source to contact substantially all surfaces of the portable electronic device comprising said raised projections.

14. The sanitizer of claim 13, wherein the controller interfaces with a sensor in the cradle to determine a presence or absence of the portable electronic device in the cradle.

15. The sanitizer of claim 14, wherein the sensor includes a weight sensor.

16. The sanitizer of claim 12, wherein the cradle is pivotable relative to the base or the cover between a first position when the sanitizer is open and a second position when the sanitizer is closed, the second position locating the cradle in the cavity between the cover and the base.

17. The sanitizer of claim 12, further comprising:
 an actuating mechanism for facilitating receipt and removal of a portable electronic device with respect to the cradle, the actuating mechanism causing in sequence:
  the cover to pivot from a closed position to an open position with respect to the base;
  the cradle to pivot from a stowed position to an exposed position with respect to the cavity; and
  the cover to pivot from the open position to the closed position with respect to the base, such that the cradle remains in the exposed position.

18. The sanitizing device of claim 17, wherein the actuating mechanism further causes in sequence:
 the cover to pivot from the closed position to the open position with respect to the base;

the cradle to pivot from the exposed position to the stowed position with respect to the cavity; and the cover to pivot from the open position to the closed position with respect to the base, such that the cradle remains enclosed in the cavity in the stowed position.

19. The sanitizer of claim 1, further comprising:
a mechanism for ejecting the portable electronic device when the cover is moved from the closed position to the open position.

20. The sanitizer of claim 1, further comprising:
a connector within said cavity for providing either or both electrical power and a data connection to the portable electronic device.

21. The sanitizer of claim 1, further comprising:
an indicator strip located at a junction between at least a portion of the base and the cover, the indicator strip being at least partially translucent to visible light and appearing illuminated when the cover is in the closed position and the ultraviolet radiation source is activated.

22. The sanitizer of claim 1, further comprising an indicator located on the sanitizer and adapted to be activated when the cover is in the closed position and the ultraviolet radiation source is activated so as to provide a visual indication that the sanitizer is on.

23. The sanitizer of claim 22, wherein the indicator is at least one LED and wherein the LED is pulsed by the controller during activation of the ultraviolet light source.

24. A sanitizer for sanitizing, a portable electronic device, the sanitizer comprising:
a base including a cavity for receiving the electronic device, wherein at least a portion of the cavity is lined with a reflective surface;
at least one ultraviolet radiation source for emitting ultraviolet radiation into the cavity;
a cover cooperating, with the base, the cover moving between an open position wherein the electronic device can be inserted into or removed from the cavity and a closed position wherein the cavity is enclosed so as to maintain the ultraviolet radiation within the cavity;
a cradle for supporting the portable electronic device within the cavity, the cradle being pivotable from a stowed position to an exposed position where at least a portion of the cradle is positioned outside of the cavity;
a first sensor for sensing whether the cover is in a closed position; and
a controller for controlling activation of the ultraviolet radiation source when the first sensor senses that the cover is closed, the controller activating the ultraviolet radiation source for a first predetermined period of time.

25. The sanitizer of claim 24, wherein the first sensor comprises a contact on the base and a mating contact on the cover, the contacts completing a circuit.

26. The sanitizer of claim 24, wherein the controller includes a manual switch that controls activation of the ultraviolet radiation source.

27. The sanitizer of claim 24, further comprising an indicator strip located at a junction between at least a portion of the base and the cover, the indicator strip being at least partially translucent to visible light produced by the ultraviolet light source so as to appear illuminated when the cover is in the closed position and the ultraviolet radiation source is activated.

28. The sanitizer of claim 24, wherein the ultraviolet radiation source is a fluorescent tube.

29. The sanitizer of claim 24, wherein the ultraviolet radiation source includes at least one light emitting diode.

30. The sanitizer of claim 24, wherein the second sensor includes a weight sensor.

31. The sanitizer of claim 24, further comprising a second sensor for sensing the presence or absence of a portable electronic device within the cavity;
wherein the controller activates the ultraviolet radiation source for the first predetermined period of time when the second sensor senses the presence of a portable electronic device within the cavity.

32. A sanitizer for sanitizing a portable electronic device, the sanitizer comprising:
a base including a bottom and side walls, a cavity for receiving the electronic device is formed within the side walls;
at least one ultraviolet radiation source for emitting ultraviolet radiation into the cavity;
a cover cooperating with and hingedly attached to the base, the cover moving between an open position wherein the electronic device can be inserted into or removed from the cavity and a closed position wherein the cavity is enclosed so as to substantially maintain the ultraviolet radiation within the cavity;
a controller for enabling the ultraviolet radiation source to be activated only when the cavity is enclosed;
an aperture from the exterior to the interior of said base which permits a cord for providing either or both electrical power and a data connection to the portable electronic device to extend out of the housing; and
a plurality of projections in the base for supporting the electronic device in the cavity spaced apart from the bottom.

33. The sanitizer of claim 32, further comprising:
a connector on a cord passing through the aperture for providing either or both electrical power and a data connection to the portable electronic device.

34. A sanitizer for sanitizing, a portable electronic device, the sanitizer comprising:
a base including a cavity for receiving the electronic device;
at least one ultraviolet radiation source for emitting ultraviolet radiation into the cavity;
a cover cooperating with the base, the cover moving between an open position wherein the electronic device can be inserted into or removed from the cavity and a closed position wherein the cavity is enclosed so as to substantially maintain the ultraviolet radiation within the cavity;
a controller for enabling the ultraviolet radiation source to be activated only when the cavity is enclosed; and
an indicator strip located on the exterior of the sanitizer at a junction between at least a portion of the base and the cover, the indicator strip being at least partially translucent to visible light and appearing illuminated when the cover is in the closed position and the ultraviolet radiation source is activated.

35. A sanitizer for sanitizing a portable electronic device, the sanitizer comprising:
a substantially rectangular base including a cavity for receiving the electronic device;
at least one ultraviolet radiation source for emitting ultraviolet radiation into the cavity;
the base including an inner bottom surface with a reflective coating, the radiation source being mount proximate to the bottom surface, the base including one or more supports for positioning the electronic device at a raised position relative to the bottom surface and above the radiation source;

a substantially rectangular cover hingedly attached to the base at one end of the base, the cover pivoting between an open position wherein the electronic device can be inserted into or removed from the cavity and a closed position wherein the cavity is enclosed so as to substantially maintain the ultraviolet radiation within the cavity, the cover having a inner top surface with a reflective coating;

a controller for enabling the ultraviolet radiation source to be activated only when the cavity is enclosed; and an indicator light located on the base or the cover, the indicator light adapted to be activated when the radiation source is emitting ultraviolet radiation into the cavity.

36. The sanitizer of claim 35, further comprising a cradle for supporting the portable electronic device, the cradle being pivotable from a stowed position to an exposed position where at least a portion of the cradle is positioned outside of the cavity for supporting the portable device.

37. The sanitizer of claim 35, further comprising an indicator strip located on at least one of the base and the cover, the indicator strip appearing illuminated when the cover is in the closed position and the ultraviolet radiation source is activated.

\* \* \* \* \*